(12) United States Patent
Brehm et al.

(10) Patent No.: US 11,696,780 B2
(45) Date of Patent: Jul. 11, 2023

(54) PAPILLOTOME FOR PERCUTANEOUS ENDOSCOPIC GASTROSTOMY

(71) Applicant: FUJIFILM MEDWORK GMBH, Höchstadt (DE)

(72) Inventors: Andreas Brehm, Adelsdorf (DE); Matthias Stirnweiss, Lonnerstadt (DE); Jörg Klyeisen, Heroldsbach (DE); Arno Dormann, Cologne (DE)

(73) Assignee: FUJIFILM MEDWORK GMBH, Höchstadt (DE)

( * ) Notice: Subject to any disclaimer, the term of this patent is extended or adjusted under 35 U.S.C. 154(b) by 902 days.

(21) Appl. No.: 16/573,838

(22) Filed: Sep. 17, 2019

(65) Prior Publication Data
US 2020/0008832 A1    Jan. 9, 2020

Related U.S. Application Data

(62) Division of application No. 15/317,321, filed as application No. PCT/EP2015/061150 on May 20, 2015, now Pat. No. 10,543,011.

(30) Foreign Application Priority Data

Jun. 10, 2014 (DE) .................... 10 2014 211 048.3
Sep. 9, 2014 (DE) .................... 10 2014 112 985.7

(51) Int. Cl.
*A61B 17/32* (2006.01)
*A61B 17/3205* (2006.01)
(Continued)

(52) U.S. Cl.
CPC ............... *A61B 17/320016* (2013.01); *A61B 17/32056* (2013.01); *A61B 18/14* (2013.01);
(Continued)

(58) Field of Classification Search
CPC ........ A61B 18/1492; A61B 2018/1407; A61B 2018/144; A61B 2018/00553;
(Continued)

(56) References Cited

U.S. PATENT DOCUMENTS

| 2,008,525 A | 7/1935 | Wolber et al. |
| 4,181,131 A | 1/1980 | Ogiu |

(Continued)

FOREIGN PATENT DOCUMENTS

| DE | 2426781 A1 | 12/1975 |
| DE | 2657256 A1 | 6/1978 |

(Continued)

OTHER PUBLICATIONS

Cyrany J. et al.; New technique for release of a buried bumper . . . ; Endoscopy 2012; 44; E422-E423.

*Primary Examiner* — Dianne Dornbusch
(74) *Attorney, Agent, or Firm* — Lucas & Mercanti, LLP; Klaus P. Stoffel

(57) ABSTRACT

A papillotome for percutaneous endoscopic gastrostomy including a front opening located in a free end region of a catheter and at the outlet of a first lumen, a rear opening further from a free end than the front opening and connects the first lumen to the outside, and a cutting wire located in the first lumen in an axially displaceable manner and extends through the front opening and the rear opening and is located on the outside between the front opening and the rear opening. When the cutting wire is tensioned, the free end region is deformed in an arc shape and the cutting wire forms a transversely extending cutting edge between the front opening and the rear opening. The front opening is arranged at a distance of at least 3 mm from the free end. A projection is formed between the free end and the front opening. A cutting tip is formed at the free end of the (Continued)

catheter. The cutting tip is connected to the cutting wire and forms the foremost end of the papillotome.

7 Claims, 6 Drawing Sheets

(51) Int. Cl.
 *A61B 18/14* (2006.01)
 *A61B 18/00* (2006.01)
(52) U.S. Cl.
 CPC ............. *A61B 2018/00494* (2013.01); *A61B 2018/00601* (2013.01); *A61B 2018/144* (2013.01)
(58) Field of Classification Search
 CPC .... A61B 2018/00601; A61B 17/32056; A61B 17/3207; A61B 2017/320733
 See application file for complete search history.

(56) References Cited

U.S. PATENT DOCUMENTS

| | | | | |
|---|---|---|---|---|
| 4,325,374 | A * | 4/1982 | Komiya | A61B 18/14 606/47 |
| 4,846,175 | A | 7/1989 | Frimberger | |
| 5,024,617 | A * | 6/1991 | Karpiel | A61B 18/14 606/47 |
| 5,163,938 | A | 11/1992 | Kambara | |
| 5,396,902 | A | 3/1995 | Brennen | |
| 5,810,807 | A * | 9/1998 | Ganz | A61B 18/1492 606/113 |
| 5,967,984 | A * | 10/1999 | Chu | A61B 8/12 600/439 |
| 6,017,340 | A * | 1/2000 | Cassidy | A61B 18/14 606/110 |
| 6,471,702 | B1 * | 10/2002 | Goto | A61B 18/14 606/46 |
| 7,648,502 | B2 * | 1/2010 | Jacques | A61B 17/32056 606/167 |
| 9,039,661 | B2 | 5/2015 | Becker et al. | |
| 2002/0068879 | A1 * | 6/2002 | Lubock | A61B 10/0266 600/567 |
| 2003/0108853 | A1 | 6/2003 | Chosack | |
| 2007/0100337 | A1 * | 5/2007 | Kawahara | A61B 18/1492 606/46 |
| 2007/0282358 | A1 | 12/2007 | Remiszewski | |
| 2008/0091196 | A1 | 4/2008 | Deal | |
| 2008/0109022 | A1 | 5/2008 | Sherwood et al. | |
| 2009/0048487 | A1 * | 2/2009 | Yanuma | A61B 18/1492 600/139 |
| 2010/0029863 | A1 | 2/2010 | O'Lenick et al. | |
| 2010/0298634 | A1 * | 11/2010 | Yanuma | A61B 17/22 600/104 |
| 2012/0302962 | A1 | 11/2012 | Becker | |
| 2014/0243822 | A1 | 8/2014 | Farin | |
| 2014/0276949 | A1 | 9/2014 | Staunton | |
| 2017/0143363 | A1 | 5/2017 | Dormann | |

FOREIGN PATENT DOCUMENTS

| | | |
|---|---|---|
| DE | 2808546 A1 | 8/1978 |
| DE | 3643362 A | 6/1988 |
| DE | 9409072 U1 | 10/1994 |
| DE | 102011085721 A1 | 5/2013 |
| WO | 2012160134 A1 | 11/2012 |
| WO | 2015189017 A1 | 12/2015 |

* cited by examiner

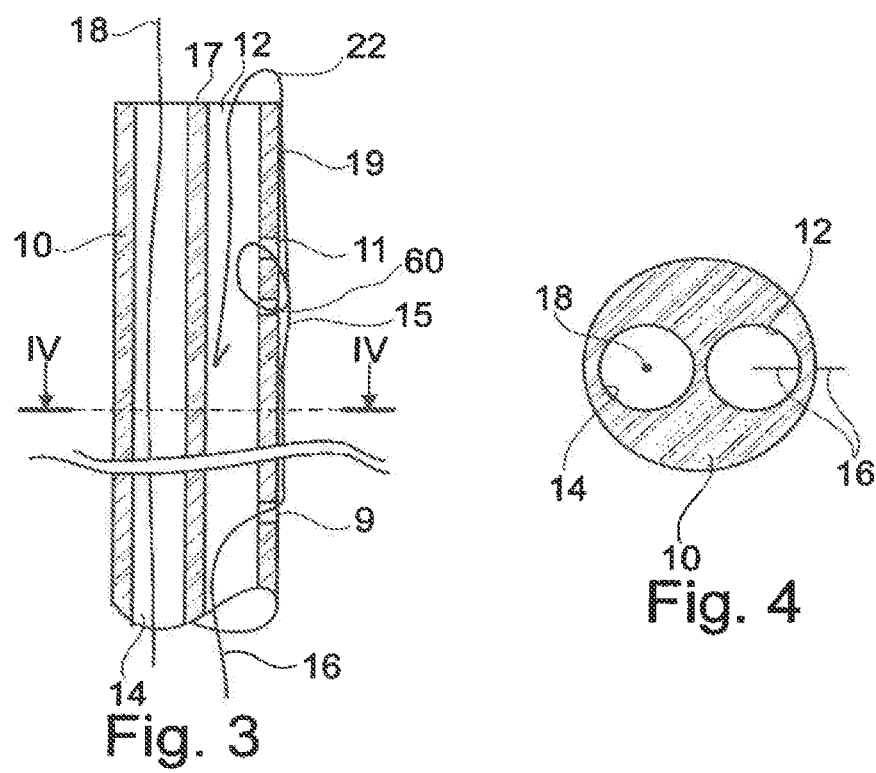
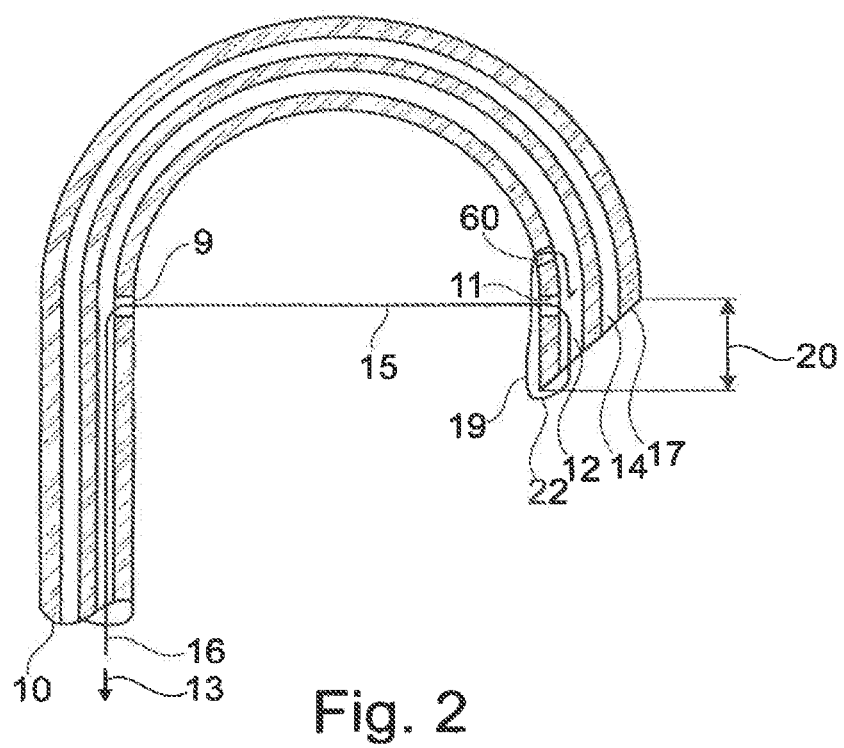

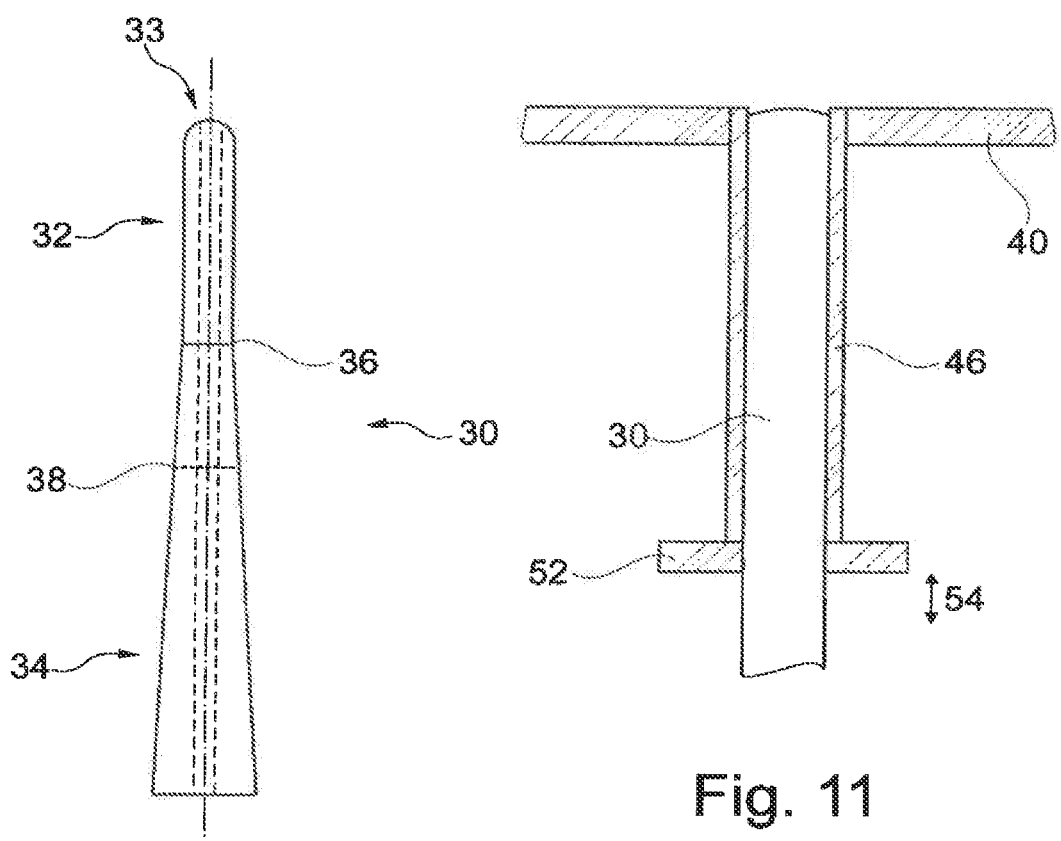

PAPILLOTOME FOR PERCUTANEOUS ENDOSCOPIC GASTROSTOMY

The present application is a Divisional Application of U.S. patent application Ser. No. 15/317,321, filed Dec. 8, 2016, which is a 371 of International Application PCT/EP2015/061150 filed on May 20, 2015 which claims the benefit of priority from German Patent Application No. 10 2014 112 985.7 filed Sep. 9, 2014 and German Patent Application No. 10 2014 211 048.3 filed Jun. 10, 2014, the contents of each of which are incorporated herein by reference.

BACKGROUND OF THE INVENTION

The invention relates to a papillotome for percutaneous endoscopic gastrostomy (PEG) and methods for using the papillotome. In one embodiment, the papillotome comprises a) a handle, b) an elongate flexible catheter attached to the handle, which has a free end region with a free end and has at least one first lumen, c) a front opening, which is located in the free end region and connects the first lumen to an outside of the catheter, d) a rear opening, which is located in the free end region and is further from the free end than the front opening and which connects the first lumen to the outside, wherein the front opening and the rear opening are arranged with the same orientation to the catheter, and e) a cutting wire, which is located in an axially displaceable manner in the first lumen, extends through the front opening and the rear opening, is located between the front opening and the rear opening on the outside, and which is fixed in the free end region and in the handle, wherein, when the handle is actuated, the cutting wire is tensioned, the free end region is deformed in an arc shape and the cutting wire forms a transversely extending cutting edge between the front opening and the rear opening. It further relates to a method for removing an ingrown PEG bumper and the use of the papillotome for the percutaneous endoscopic gastrostomy for removing an ingrown PEG bumper, referred to as buried bumper.

Papillotomes are generally described in German patents DE 36 43 362 A 1, DE 26 57 256 A1 and DE 94 09 072 U1. They are endoscopically inserted into the patient's body. In particular, they are provided for removing gallstones. They are also referred to as loop papillotomes.

In known papillotomes, a front opening is located at the free end of the catheter. The cutting wire exits at this free end and, until the second opening, is located at the outside of the catheter. By actuating the handle, the cutting wire is displaced relative to the catheter, and the catheter is bent or deformed in a U-shape between the front and a second, rear opening. The cutting wire directly connects the front opening to the second opening. A loop is formed between the cutting wire and the bent free end region of the catheter. The cutting wire is connected to a high-frequency (HF) voltage source. Cutting can be performed in the known manner and in accordance with the prior art. The cutting path is determined by the movement of the catheter.

Loop papillotomes of this type have proved themselves especially for endoscopic application, in particular for removing gallstones. In the process, the papilla vaterie or the musculus sphincter oddi are severed. Tissue protruding over a certain extent can be cut through.

A buried bumper syndrome is an ingrown PEG bumper of a PEG tube. In the case of a PEG tube, a tube is inserted into the stomach of a patient through the abdominal wall and the stomach wall (percutaneously). The patient is provided with food and liquid via this tube. The PEG tube has a PEG catheter. The latter is connected outside the body with a connection system of the PEG tube, which is then connected via the PEG catheter to the inside of the stomach. The PEG catheter extends through the abdominal wall and the stomach wall. In the case of insufficient or improper care, the PEG bumper may be enclosed and overgrown by the stomach wall. This is referred to as the buried bumper syndrome.

According to the prior art, ingrown PEG bumpers are removed by laparotomy, by means of the pull method or the push method.

Laparotomy is understood to mean the surgical opening of the abdominal wall. Within the course of this operation, the stomach wall is also opened and the ingrown PEG bumper is cut free from outside. This is a laborious, very invasive and therefore risky operation that is used only in rare cases.

The pull method is based on freeing the ingrown PEG bumper from the tissue by pulling from the outside, after prior incision into the surrounding tissue. A biopsy forceps is inserted through the positioned PEG catheter in order to render it rigid and is then opened for resistance. By pulling on the biopsy forceps, the abdominal wall bulges at the location of the ingrown PEG bumper. The abdominal wall and a part of the stomach wall in the direct vicinity of the PEG catheter are cut through down to the PEG bumper. Then, the PEG bumper is pulled free to the outside by pulling from the outside with the biopsy forceps. This method is less invasive than a laparotomy, but a part of the abdominal wall and the stomach wall is still cut through also in this case; this entails the risks connected therewith.

In the push method, the PEG bumper is cut free from inside, i.e. from the inside of the stomach, under endoscopic monitoring. For this purpose, a cutting tool is endoscopically or percutaneously inserted into the inside of the stomach and the PEG bumper is laid open. Most frequently, needle papillotomes are used for this purpose; they have a needle-like cutting tool at their tip with which the tissue can be cut. Most frequently, they are introduced endoscopically. Loop papillotomes may also be used; they are introduced percutaneously via the PEG catheter. For this purpose, they are advanced through the PEG catheter in a relaxed, not bent, state. Once the papillotome catheter has been advanced into the inside of the stomach (stomach lumen) to a sufficient extent, the handle is actuated and the papillotome loop is thus formed. By pulling back the catheter, the cutting wire is pulled back onto the tissue surrounding the PEG bumper; the former can now be cut until the cutting wire comes up to the PEG bumper. Most frequently, several of these radial incisions are made until the PEG bumper is laid open. Then, the PEG bumper is pressed into the inside of the stomach with a standard bougie, also referred to as a dilator, which has been advanced through the PEG catheter. The freed PEG bumper can then be removed endoscopically.

Bougies are medical instruments from stainless steel or other hard materials with a conical shape that dilate body orifices or vessels.

The push method is the least invasive method and affords the lowest rate of complications of the methods presented. However, problems and complications arise also in this case. The disadvantages of the push technique are a frequently occurring slipping or shifting of the loop of the papillotome when pulling it back onto the PEG bumper; this triggers more substantial bleeding, larger seats of infection and a greater amount of work. Furthermore, the PEG bumper cannot be laid open laterally. The existing bougies are not designed for application with and for a PEG tube.

SUMMARY OF THE INVENTION

Based on this, it is an object of the invention to develop the push method and to provide a device and a method with which the procedure can be performed in a more targeted and simpler manner, a slipping of the papillotome is prevented and the incisions can be made in a more targeted manner.

This object is achieved with a device that, in addition to the abovementioned features, also includes the following features: The front opening is disposed at a distance of at least 3 mm from the free end, and a projection is formed between the free end and the front opening, the cutting wire is furthermore located between the free end and the front opening on the outside, and there forms a longitudinally extending cutting edge disposed with the same orientation to the catheter as the front opening and the rear opening.

Because of the projection, the cutting wire does not start directly at the free end of the free end region of the catheter, but at a distance from the free end. Thus, the projection can serve as a stop. After the free end region has been introduced into the inside of the stomach, the free end region is still substantially rectilinear. If the handle is now actuated and the free end region is bent thereby, the projection abuts against a lateral edge of an overgrowth of the PEG bumper. This results in a defined and—to a certain extent—fixed position of the projection. At its free end region, the papillotome acts like a forceps; a clamping action takes place between the projection and the catheter, beyond the rear opening. The part of the PEG bumper located there is crossed and clamped. Thus, the cutting wire is supported and fixed &so in the vicinity of the front opening. It is not retained solely by the catheter itself. If the surgeon now pulls the catheter outwards and makes an incision, then it is not just the part of the transversely extending cutting edge which is located in the vicinity of the second opening that cuts where the tensioning acts in particular, but also that part of the cutting edge that is located in the vicinity of the front opening, because the above-described support is provided there. In particular, the longitudinally extending cutting edge, which is located outside the jacket of the disc-shaped PEG bumper, also cuts. By further pulling on the cutting wire, the loop can be made smaller, and thus the effect of the longitudinally extending cutting edge can be controlled. By pulling on the catheter, the action of the transversely extending cutting edge can be influenced.

The cutting wire protrudes outwards in relation to the free end. This region of the cutting wire forms a cutting tip. In addition, this also serves the following purpose: Depending on the extent the PEG bumper is overgrown, it may happen that the inner opening of the PEG catheter into the inside of the stomach is overgrown. In these cases, the overgrowth is loosened and cut through with the front cutting tip when introducing the catheter. Thus, the way into the inside of the stomach can be cut free. The free end region of the papillotome is only then located in the gastric lumen. Moreover, the cutting tip allows hooking into the stomach wall after or during the bending of the papillotome. This also prevents a slipping of the free end region. Such slipping can also take place when the catheter is pulled back. An uncontrolled cutting of the cutting wire into the overgrowth is prevented, or at least made more difficult. Non-targeted and careless cuts, larger wounds, and thus avoidable bleeding and seats of infections are avoided.

The cutting tip may also be formed by a sphere. The sphere is attached to the catheter and electrically connected to the cutting wire. The diameter of the sphere is selected to be as small as possible; it is slightly larger than the clear diameter of the first lumen. Thus, the sphere remains outside the first lumen.

The longitudinally extending cutting edge is preferably formed by the cutting wire itself. However, it may also be formed by a needle, as is the case with the needle papillotome. A metal piece, which forms at least a part of the transversely extending cutting edge, may also be introduced into the first lumen. It is indeed possible and provided that the cutting tip is located at a certain distance of e.g. 1-8 mm from the free end of the catheter, i.e. freely protrudes from the first lumen by that extent.

The projection may be formed only by a region of the catheter. It may be at least partially formed by a metal piece that is mechanically connected to the catheter. The projection may be a hybrid; in that case, the projection is defined in part by a region of the catheter, in part by a metallic article that protrudes from the free end.

The transversely extending cutting edge and the longitudinally extending cutting edge have the same orientation to the catheter. This means the following: If one looks at the catheter in the axial direction, the two openings are located in the same angular position. Thus, the cutting wire of both cutting edges is also located in the same angular position.

Preferably, the free end of the catheter has a bevel. The angle of the bevel is, in particular, about 45°; a deviation by ±20° is possible. A tip is formed by the bevel. This tip preferably has the same orientation to the catheter as the front opening and the rear opening.

The length of the overgrowth preferably corresponds to at least the thickness of the PEG bumper used. This length is adapted to the thickness. In the case of thin bumpers, the projection can be chosen to be smaller, and correspondingly larger in the case of thick bumpers. The thickness of the overgrowth, which, however, is not always known, must be added to this.

Preferably, a third opening is formed in the catheter. It is located between the front opening and the rear opening. It is in the immediate vicinity, in particular 1 to 8 mm, of the front opening. It is orientated just like the two other openings. The wire that forms the longitudinally extending cutting edge can be introduced into the catheter or guided out from it through the third opening. The longitudinally extending cutting edge can be formed in such a way that it forms an intersection with the transversely extending cutting edge. Thus, cutting is improved where the two cutting edges converge. The front opening is preferably used only for the wire that forms the transversely extending cutting edge.

The transversely extending cutting edge may also be formed by a rope. A rope is advantageous in that, in the bent state of the free region, it extends substantially straight between the two openings. In the case of a cutting wire that has only one filament, this is not always fully accomplished. It is also possible to form the cutting edge by a thin, rigid metal pin that is not deformable, and which is formed, for example, to be similar to a sewing needle. Its length must be dimensioned such that, in the case of the strongest, intended bending of the free end region, it is no longer than the distance between the two openings. Such a non-deformable cutting edge is advantageous in that it yields less during a cutting process than a wire. It may also be formed by a metal tube that is pushed over the cutting wire and has the length of the metal pin.

Preferably, the handle is formed such that the catheter is connected to a stationary part of the handle, while a movable, in particular displaceable, part of the handle is connected to the cutting wire. If the displaceable part is then pulled outwards, the bend is created. Preferably, the handle has a locking device. By means of that, the position of the movable part of the handle can be locked into place in relation to a stationary part of the handle.

A locking mechanism of the locking device prevents a bending or extension of the PEG loop papillotome or renders it more difficult. This locking mechanism can be configured to be continuous. Alternatively, the locking mechanism may be graduated. For example, it may be one or more catches with a depression or a catch with several depressions. Several catches with several depressions may also be used. The locking mechanism can be adapted to a radius of the PEG bumper. When the PEG papillotome is applied, it is bent, as was explained above with respect to already existing loop papillotomes, in order to form the loop or the transversely extending cutting edge. By means of the locking mechanism, the PEG loop papillotome can be prevented from extending again during cutting, due to the resistance of the tissue. A mechanical tension can be maintained in the bent loop, so that the projection abuts in a nonpositive manner.

The catheter preferably has a length of between 40 and 150 cm, preferably of 50 to 120 cm. Commercially available papillotomes are formed to be much longer because they may be introduced endoscopically and designed for the bile duct. A smaller length facilitates unimpeded operation. In the known manner, the catheter is manufactured from, for example, polytetrafluoroethylene. It has a diameter of 2 to 4 mm. Preferably, it has two lumina; the second lumen is used for a guidewire; such a wire is useful in a push method.

The invention also includes a PEG bougie. In one embodiment, the PEG bougie comprises a hard main body whose outer diameter is adapted to the inner diameter of the PEG catheter or of the PEG bumper. The main body of the PEG bougie is configured to be either conical or having a constant outer diameter, which substantially corresponds to the clear inner diameter of the PEG catheter. The PEG bougie may have a softly rounded, yielding tip with a first length that is made from a different material than the main body.

Due to the soft forward section with a rounded tip, it is ensured that the PEG bougie does not damage the opposite stomach wall during the introduction into the inside of the stomach. A possible existing longitudinal channel is designed in such a way that the guidewire can be introduced, so that the PEG bougie can be introduced into the PEG catheter and the inside of the stomach in a targeted manner. What is important is that the PEG bougie has no edges over the longitudinal extent, so that it may not get caught in the PEG catheter. The conical profile nevertheless ensures that the PEG bumper is pressed out into the inside of the stomach. The pitch number specifies the ratio of the second diameter to the first diameter.

The PEG bougie can be manufactured by means of the co-extrusion method.

The diameter of the tip or of the forward section is preferably between 30 and 90% of the inner diameter of the PEG catheter.

The forward section preferably has a length of between three and eight cm, particularly preferably between four and six cm. The PEG bougie preferably has an overall length of between 10 and 24 cm, particularly preferably between 13 and 18 cm.

The pitch number is preferably selected in such a way that the main body has the inner diameter of the PEG bumper after one to six cm, particularly preferably after two to four cm.

Furthermore, the invention also includes a method for removing an ingrown PEG bumper with a PEG papillotome and a PEG bougie according to the present invention. In one embodiment, the method for cutting the PEG bumper free comprises the following steps:
a) introducing a guidewire through the PEG catheter into an inside of the stomach, b) introducing the guidewire into the second lumen of the PEG papillotome c) introducing the PEG papillotome along the guidewire through the PEG catheter into the inside of the stomach, d) positioning the PEG papillotome so that a bending of the PEG papillotome results in a contact between the stomach wall and the cutting tip, e) bending the PEG papillotome by actuating the handle until the projection abuts the overgrowth outside the circumference of the PEG bumper and the cutting tip touches the stomach wall, f) cutting into the tissue laterally surrounding the PEG bumper with the longitudinally extending cutting edge and by further bending the PEG papillotome, using an HF cutting current, until the longitudinally extending cutting edge of the PEG papillotome comes up against the PEG bumper, g) cutting into the tissue enclosing the PEG bumper on top with the transversely extending cutting edge by pulling back the PEG papillotome, using an HF cutting current, until the horizontal cutting edge of the PEG loop papillotome comes up against the PEG bumper, wherein the steps f) and g) can also be carried out in a different sequence and at least partially at the same time, h) pushing the PEG loop papillotome back into the inside of the stomach and repositioning the PEG papillotome at a different location, i) repeating the steps e) to h) one to several times, and k) removing the PEG papillotome from the inside of the stomach and the PEG catheter.

In one embodiment, the ingrown PEG bumper, which has been cut free, is removed by a method comprising the steps of:
l) introducing a PEG bougie through the PEG catheter at least up to the vicinity of the PEG bumper, m) luxating the PEG bumper from the cut tissue into the inside of the stomach by means of pressure on the PEG bougie, n) positioning an endoscopically introduced loop around the bumper, o) detaching the PEG bumper from the PEG bougie by means of tension on the loop, p) endoscopically removing the PEG bumper and the PEG catheter located thereon, and q) removing the PEG bougie.

Other advantages and features of the invention will be apparent to one skilled in the art from the claims and the description below of several exemplary embodiments of the invention, which shall be understood not to be limiting. The exemplary embodiments are explained in more detail below with reference to the description and the drawings:

BRIEF DESCRIPTION OF THE DRAWINGS

FIG. 2: shows an axial sectional view through the free end region of the catheter according to FIG. 1, FIG. 3: shows an axial sectional view similar to FIG. 1 through the free end region of the second exemplary embodiment, FIG. 4: shows a radial section along the line of cut IV-IV in FIG. 3, FIG. 5: shows a sectional view similar to FIG. 2 for a third exemplary embodiment, now with a rigid metal body that, in part, forms the projection, FIG. 10: shows a side view of a first embodiment of a bougie, and FIG. 11: shows a side view of a second embodiment of a bougie.

DETAILED DESCRIPTION OF THE INVENTION

Figure 1:
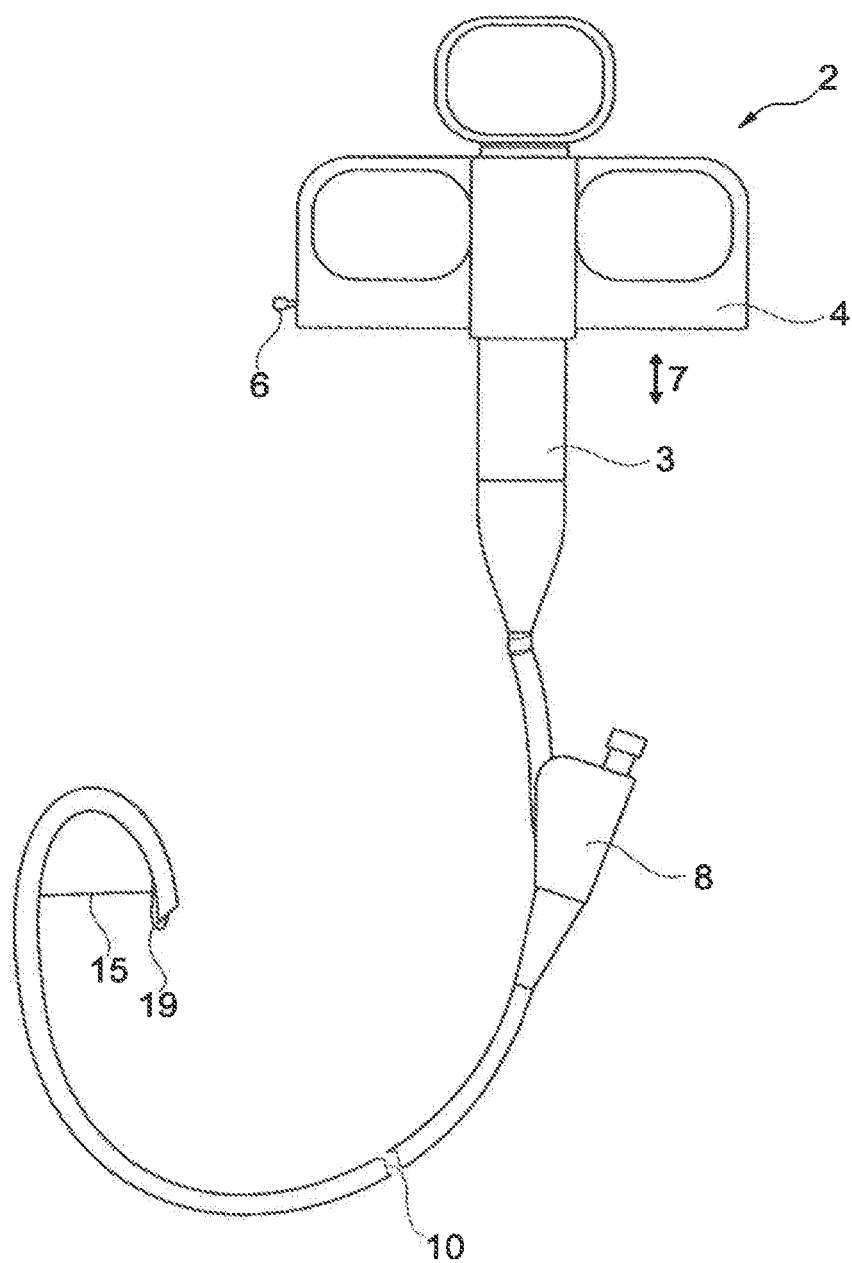
FIG. 1: shows a top view of a first exemplary embodiment of a papillotome with a bent free end region; both cutting edges can be seen.

The papillotome has a handle 2 with a stationary part 3 and a movable part 4, which here is configured as a slider that is displaceably guided on the stationary part 3. The stationary part 3 has an eyelet; two corresponding openings are provided on the movable part 4. A finger or a thumb can be inserted into all of them; the movable part can be displaced by moving. An HF terminal 6 is provided on the movable part 4. The movement is illustrated by the arrow 7. At the lower end of the stationary part 3, the latter transitions into a catheter 10. It is configured with two lumina, see FIG. 4. A second lumen 14 is accessible via a base 8. The latter ends with a screw thread. A guidewire 18 can be introduced here.

The catheter 10 has a free end region. This extends from a foremost tip of the papillotome to a small extent beyond a rear opening 9. The front end region is the part of the catheter 10 which can be transferred from an extended into a bent state; the bent state is shown in FIG. 1.

Details of the free end region are apparent from FIG. 2. A cutting wire 16 is displaceably guided in a first lumen 12. It is connected to the movable part 4 and the HF terminal 6. In the bent state as it is shown in FIG. 2, a tensile force acts on the cutting wire 16 in accordance with the arrow 13. The cutting wire 16 is stretched between the rear opening 9 and a front opening 11; there, it extends as straight as possible; it forms a transversely extending cutting edge 15. After passing the front opening 11, the cutting wire 16 runs in the first lumen 12 towards a free end 17; there, it exits the first lumen 12 and is bent around the end of the tube of the catheter 10 located there. It is routed along the outside. It reenters the first lumen 12 through a third opening 60. The third opening 60 is located between the front opening 11 and the rear opening 9. It is a very short distance away from the front opening 11. The distance is in the range of 1 to 8 mm. The third opening 60 is orientated to the catheter 10 as the two other openings 9, 11 are. After penetrating the third opening, the cutting wire 16 is inserted deeper into the first lumen 12 and possibly secured by an angled portion (as drawn).

In a second embodiment according to the FIGS. 3 and 4, the free end is not cut off at an acute angle, as is apparent particularly from FIG. 2, but is cut off at the angle of 90°. The angle according to FIG. 2 can be between 10 and 80°; preferably, it is 45°. A guide wire 18 is introduced into the second lumen 14. The course of the cutting wire 16 is similar to the first exemplary embodiment, but with the following difference: After passing the front opening 11, the cutting wire 16 runs in the first lumen 12 towards the rear opening 11 and exits the first lumen 12 at the third opening 60 and is bent around the free end 17 of the tube of the catheter 10 and inserted into the first lumen 12. There, it has an arbitrary length. It is possibly secured by an angled portion. The latter can be hooked in with a short piece between the front opening 11 and the third opening 60 of the cutting wire 16 or the piece of the cutting wire 16 beyond the rear opening 9.

The length of the projection 20 in the first exemplary embodiment is virtually equal to the length between an intersection of the longitudinally extending cutting edge 19 with the transversely extending cutting edge 15 and a cutting tip 22. To be exact, the projection 20 is slightly longer than the distance between the front opening 11 and the free end, because the cutting wire 16 is bent around the end of the tube of the catheter 10 and there adds to the length of the projection. At its direction-changing portion at the tip of the free end 17, the cutting wire 16 forms the cutting tip 22.

Figure 5:
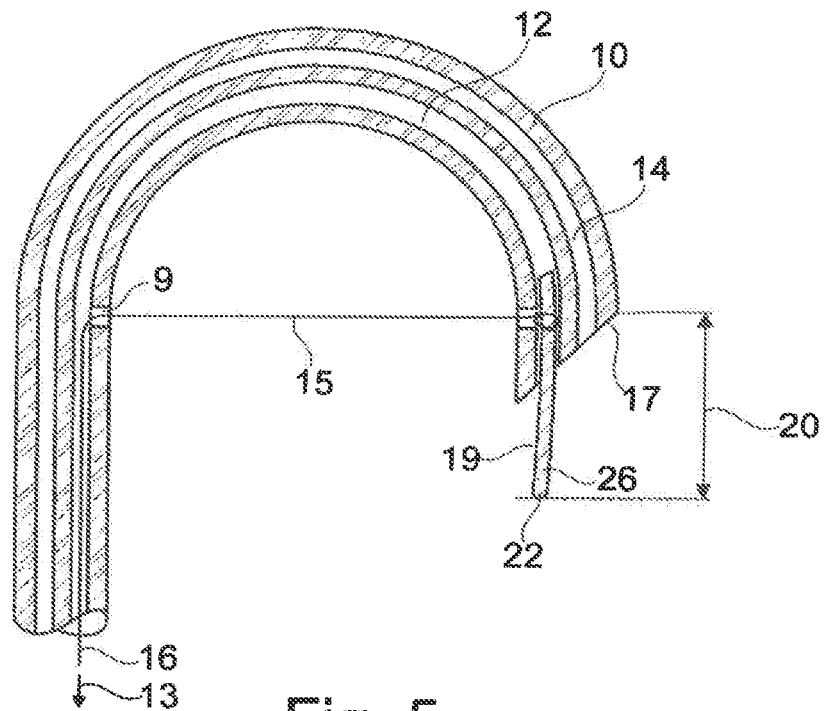

In a third exemplary embodiment according to FIG. 5, the projection 22 is defined in part by a section of the catheter 10 protruding over the front opening 11 and in part by a metal piece 26, which is substantially configured as a needle. This metal piece 26 has an outer diameter that approximately corresponds to the clear diameter of the first lumen 12. The metal piece 26 is not flexible; it has the strength of, for example, a sewing needle. It is electrically connected to the cutting wire 16. The cutting wire is laid around the needle 26 and protrudes from the front opening 11 towards the outside; as in the previous exemplary embodiments, it extends to the rear opening 9 while forming a transversely extending cutting edge 15. The cutting tip 22 is now formed by the outside tip of the metal piece 26. The longitudinally extending cutting edge 19 now no longer extends over the entire length of the projection 22 but only over a part of the projection 22, for example maximally 80%, preferably maximally 60%.

Figure 6:
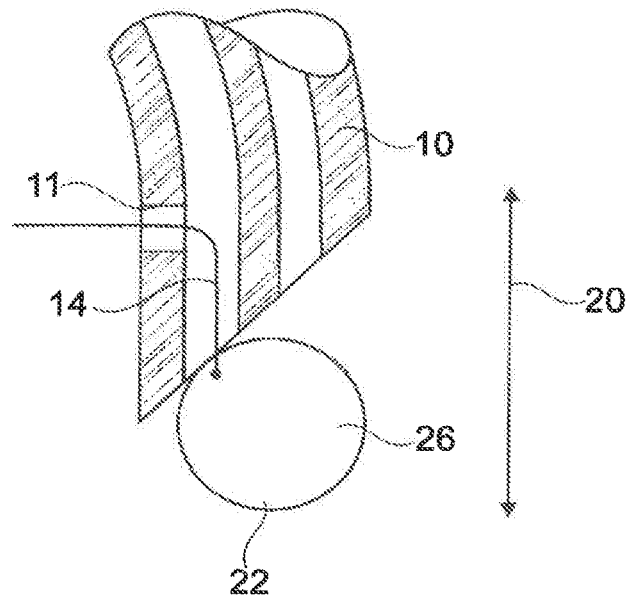
FIG. 6: shows an axial sectional view of a section of the free end region, now with a sphere at the free end of a first lumen; the rest is configured as in FIG. 5, FIG. 7: shows a schematic view of a section of the free end region similar to FIG. 5, now with a different metal body.

In a fourth exemplary embodiment according to FIG. 6, the metal piece 26 is formed by a sphere forming the cutting tip 22. It is electrically connected to the cutting wire 16. It is placed on the end of the second lumen 14 and attached there.

Figure 7:
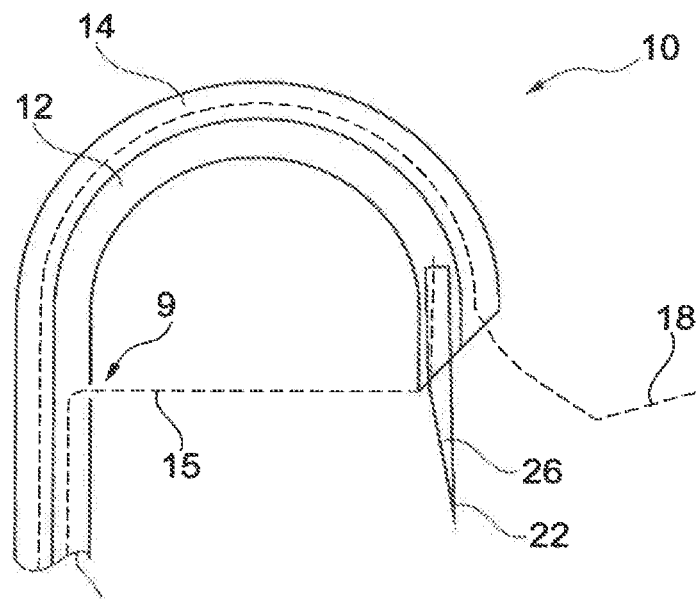

In a fifth exemplary embodiment according to FIG. 7, the metal piece 26 is configured as a knife that cuts by itself. It is possible to selectively cut with the knife with or without an HF voltage applied to the knife. In the first case, both the transversely extending cutting edge 15 and the knife are cutting, because the cutting wire 16 and the metal piece 26 are electrically connected. In the second case, only the knife cuts, however in a purely mechanical manner. In addition, and independent from this, the metal piece 26 alone forms the projection 20. The front opening 11 coincides with the free end of the first lumen 12. The cutting wire 16 is electrically connected to the metal piece 26.

Figure 8:
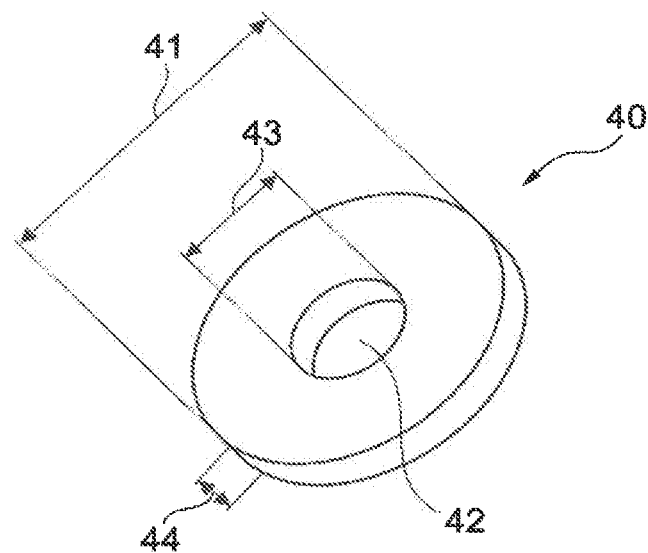
FIG. 8: shows a perspective view of a PEG bumper.

FIG. 8 shows a commercially available PEG bumper 40. It has a passage 42. It is formed as a circular disc, Its thickness is denoted 44, 41 is its outer diameter, 43 is the diameter of the hole.

Figure 9:
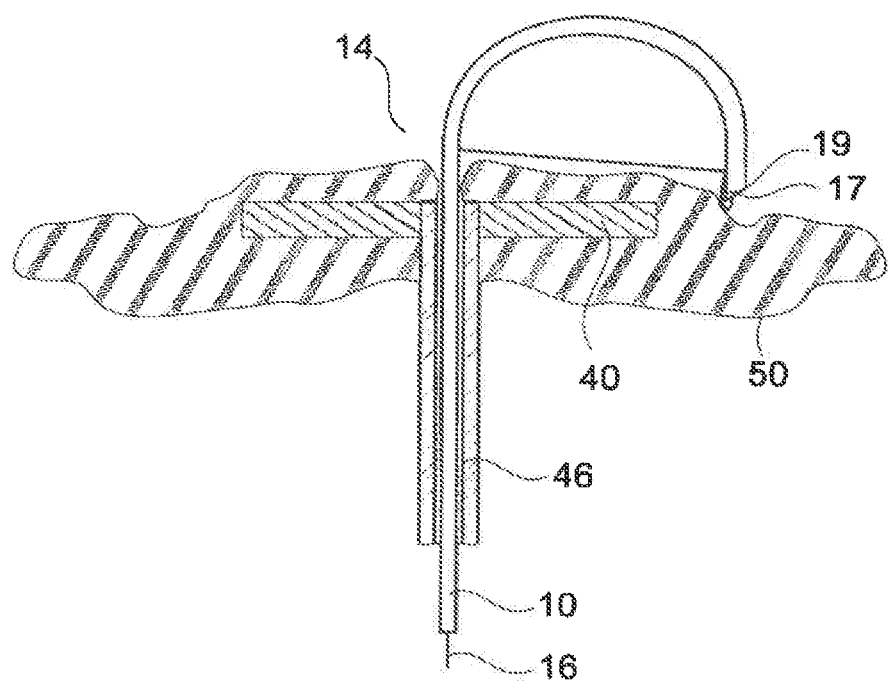
FIG. 9: shows a section through a stomach wall with an ingrown PEG bumper and a PEG catheter; a papillotome is inserted and ready to cut.

FIG. 9 shows such a PEG bumper 40 ingrown into a stomach wall 50. The PEG bumper 40 is connected to a PEG catheter 46, It can be seen that the outlet of the PEG catheter 46 inside the stomach, which has previously been overgrown by mucosa, has been opened; this was done by means of the cutting tip 22. The papillotome is already shown in a position in which a cutting process can take place. The cutting tip 22 is in contact with the mucosa; the transversely extending cutting edge 15 rests on the inside of the mucosa. The inside of the stomach is located at the top of FIG. 9. If an HF voltage is now applied to the cutting wire 16 and the catheter 10 pulled in a downward direction, then a cutting process takes place. This is carried out until the transversely extending cutting edge 15 comes into contact with the PEG bumper 40. In the process, the cutting wire 16 can be pulled still further in the direction of the arrow 13 in order to support the cutting process with the longitudinally extending cutting edge 19. This can be continued until there is a contact with the circumference of the PEG bumper 40.

Both cutting edges 15, 19 can thus be used separately and in a targeted manner. The transversely extending cutting edge 15 is controlled by a movement of the catheter 10 in the axial direction and a rotation of the catheter 10 about the axial direction. The longitudinally extending cutting edge 19 is controlled by pulling in the direction of the arrow 13 and releasing the cutting wire 16 in the opposite direction thereto.

Two exemplary embodiments of so-called PEG bougies 30 are shown in FIGS. 10 and 11. In the push method, they serve for pushing the PEG bumper 40 and the PEG catheter 46 connected with it forward into the inside of the stomach, so that the PEG bumper 40 comes free. In the process, the PEG catheter 40 is shortened to the greatest extent possible.

The bougie with the FIG. 10 has a forward section 32 and a main body 34; the forward section 32 has a constant diameter. It has a rounded tip 33. The tip is made from a soft material. It is connected flush with the main body 34 at a transition 36. There, the main body 34 has the same diameter as the forward section 32 and expands conically from the transition 36 in a downward direction.

The PEG bougie is fitted, tip 33 first, into the PEG catheter 46. The forward section has a maximum length of 5 cm. The main body has a length of, for example, 5 cm to 12 cm. At one location 38, the bougie has an outer diameter that substantially corresponds to the inner diameter 43 minus, possibly, the inner diameter of the PEG catheter 46. The bougie 30 cannot be inserted further past this location 38 without a resistance arising. If it is inserted further, the PEG bumper 40 is taken along and pushed inwards, into the inside.

Optionally, the bougie 30 has an internal bore for the guidewire 18.

Preferably, the bougie 30 is manufactured from plastic; in the process, a coextrusion procedure can be carried out.

FIG. 11 shows another embodiment of a bougie 30. The bougie 30 is designed to have a cylindrical main body 34 whose outer diameter is adapted by exactly the free inner diameter of the PEG catheter 46. The goal is to stiffen the PEG catheter 46 by the bougie 30 in such a way that, by means of the bougie 30 and the PEG catheter 46 together, a sufficiently large force can be exerted on the PEG bumper 40 to push the latter free. For this purpose, the PEG bougie 30 has a length that is greater than the rest of the length of the PEG catheter 46. Preferably, an axially adjustable stop 52, which supports the lower free end of the PEG catheter 46, is provided on the main body 34. The adjustability is illustrated by the double arrow 54.

The bougie 30 is a rotating part; a longitudinal axis is shown in FIG. 10. Typical PEG bumpers have an outer diameter 41 of 15 mm to 18 mm. The inner diameter 43 is typically about 5 mm.

Typically, the distance between the abdominal wall and the inside of the stomach is about 2 cm to 4 cm, depending on the patient. About 2 cm of the PEG catheter 46 are left to protrude from the abdominal wall. Thus, the cut PEG catheter 46 has a length of about 4 cm to 6 cm.

A papillotome for percutaneous endoscopic gastrostomy has a front opening 11 located in a free end region of a catheter 10 and at the outlet of a first lumen 12, a rear opening 9, which is further from a free end 17 than the front opening 11 and that connects the first lumen 12 to the outside, and a cutting wire 16, which is located in an axially displaceable manner in the first lumen 12, which extends through the front opening 11 and the rear opening 9, which is located between the front opening 11 and the rear opening 9 on the outside, wherein, when the cutting wire 16 is tensioned, the free end region is deformed in an arc shape and the cutting wire 16 forms a transversely extending cutting edge 15 between the front opening 11 and the rear opening 9. The front opening 11 is disposed at a distance of at least 3 mm from the free end 17. A projection 20 is formed between the free end 17 and the front opening 11. A cutting tip 20 is formed at the free end 17 of the catheter 10 that is connected to the cutting wire 16 and forms the foremost end of the papillotome.

While specific embodiments of the invention have been shown and described in detail to illustrate the inventive principles, it will be understood that the invention may be embodied otherwise without departing from such principles.

We claim:

1. A papillotome for percutaneous endoscopic gastrostomy, comprising:
   a handle;
   an elongate flexible catheter attached to the handle which has a free end region with a free end and has at least one first lumen;
   a front opening which is located in the free end region and connects the first lumen to an outside of the catheter;
   a rear opening, which is located in the free end region of the catheter, and is further from the free end than the front opening and which connects the first lumen to the outside, wherein the front opening and the rear opening are arranged with the same orientation to the catheter;
   a cutting wire, which is located in an axially displaceable manner in the first lumen, extends through the front opening and the rear opening, and is located between the front opening and the rear opening on the outside, and which is fixed in the free end region and in the handle,
   wherein, when the handle is actuated, the cutting wire is tensioned, the free end region is deformed in an arc shape and the cutting wire forms a transversely extending cutting edge between the front opening and the rear opening,
   wherein the front opening is disposed at distance of at least 3 mm from the free end, and a projection is formed between the free end and the front opening, and a cutting tip is formed at the free end of the catheter that is connected to the cutting wire and forms the foremost end of the papillotome,
   wherein the cutting wire has a portion that is also located on the outside between the free end and the front opening, the portion of the cutting wire forms the cutting tip and the longitudinally extending cutting edge, and the portion of the cutting wire is disposed with the same orientation to the catheter as the front opening and the rear opening.

2. The papillotome according to claim 1, wherein the cutting wire forms the cutting tip.

3. The papillotome according to claim 1, wherein the free end is beveled, wherein a tip of the bevel is disposed with the same orientation to the catheter as the front opening and the rear opening.

4. The papillotome according to claim 1, wherein the front opening is disposed at a distance of maximally 15 mm from the free end.

5. The papillotome according to claim 4, wherein the front opening is disposed at a distance of 5 to 10 mm from the free end.

6. The papillotome according to claim 5, wherein the front opening is disposed at a distance of 4 to 7 mm from the free end.

7. The papillotome according to claim 1, wherein the catheter is attached to a stationary part of the handle and the cutting wire is attached to a movable part of the handle.

* * * * *